US012343430B2

(12) United States Patent
Tan et al.

(10) Patent No.: US 12,343,430 B2
(45) Date of Patent: Jul. 1, 2025

(54) METHODS OF IMPROVING PHARMACEUTICAL SUBSTANCE SOLUBILIZATION AND PRODUCTS THEREOF

(71) Applicant: MUDANJIANG LINRUN PHARAMA EXCIPIENTS LLC., Mudanjiang (CN)

(72) Inventors: Zheng Tan, Beijing (CN); Jingang Wang, Beijing (CN); Chen Yang, Beijing (CN)

(73) Assignee: MUDANJIANG LINRUN PHARAMA EXCIPIENTS LLC., Mudanjiang (CN)

( * ) Notice: Subject to any disclaimer, the term of this patent is extended or adjusted under 35 U.S.C. 154(b) by 709 days.

(21) Appl. No.: 17/598,797

(22) PCT Filed: Apr. 7, 2020

(86) PCT No.: PCT/US2020/027023
§ 371 (c)(1),
(2) Date: Sep. 27, 2021

(87) PCT Pub. No.: WO2020/210205
PCT Pub. Date: Oct. 15, 2020

(65) Prior Publication Data
US 2022/0175677 A1 Jun. 9, 2022

Related U.S. Application Data

(60) Provisional application No. 62/830,740, filed on Apr. 8, 2019.

(51) Int. Cl.
| | |
|---|---|
| A61K 9/14 | (2006.01) |
| A61K 47/32 | (2006.01) |
| A61K 47/34 | (2017.01) |
| A61K 47/38 | (2006.01) |
| B29B 7/00 | (2006.01) |
| B29B 9/12 | (2006.01) |

(52) U.S. Cl.
CPC .............. *A61K 9/146* (2013.01); *A61K 47/32* (2013.01); *A61K 47/34* (2013.01); *A61K 47/38* (2013.01); *B29B 7/007* (2013.01); *B29B 9/12* (2013.01)

(58) Field of Classification Search
CPC ........ A61K 9/146; A61K 47/32; A61K 47/34; A61K 47/38; A61K 9/1682; A61K 9/0053; A61K 9/1635; A61K 9/1641; A61K 9/1652; A61K 9/1694; A61K 31/216; A61K 31/55; A61K 45/06; B29B 7/007; B29B 9/12; B29B 7/48; B29B 7/82

See application file for complete search history.

(56) References Cited

U.S. PATENT DOCUMENTS

| | | | | |
|---|---|---|---|---|
| 5,456,923 | A | * 10/1995 | Nakamichi | .......... A61K 9/1694 514/774 |
| 2010/0222311 | A1 | 9/2010 | Thommes et al. | |
| 2014/0210129 | A1 | 7/2014 | Okafor et al. | |
| 2015/0320808 | A1* | 11/2015 | Burcelin | ................ A61K 38/28 424/93.3 |
| 2018/0228730 | A1 | 8/2018 | Schiffter et al. | |

FOREIGN PATENT DOCUMENTS

| | | |
|---|---|---|
| CN | 1278164 A | 12/2000 |
| CN | 101516338 A | 8/2009 |
| CN | 101896161 A | 11/2010 |
| CN | 102188365 A | 9/2011 |
| CN | 104546666 A | 4/2015 |
| CN | 107920998 A | 4/2018 |
| WO | 1999021534 A1 | 5/1999 |
| WO | 2008016260 A1 | 2/2008 |

OTHER PUBLICATIONS

Stukelj et al. (Image-Based Investigation: Biorelevant Solubility of α and γ Indomethacin, Feb. 20, 2019) (Year: 2019).*
International Search Report and Written Opinion for International Application No. PCT/US20/27023, filed Apr. 7, 2020, mailed Jun. 16, 2020.
Tran, P., et al., Overview of the Manufacturing Methods of Solid Dispersion Technology for Improving the Solubility of Poorly Water-Soluble Drugs and Application to Anticancer Drugs, Pharmaceutics, vol. 11, No. 3, Jan. 1, 2019 (Jan. 1, 2019), p. 132.
Modi, A., et al., Enhancement of dissolution profile by solid dispersion (kneading) technique, AAPS Pharmscitech, Springer New York, New York, vol. 7, No. 3, Sep. 1, 2006, pp. E87-E92.
Extended European Search Report for European Application No. 20787731.7, filed Jun. 24, 2021 mailed Oct. 10, 2022.
Sejal, et al., melt extrusion with poorly soluable drugs, International Journal of Pharmaceuticals, Elseveier, vol. 453, No. 1, Nov. 20, 2012, pp. 233-252.

* cited by examiner

*Primary Examiner* — Lezah Roberts
*Assistant Examiner* — Abdulrahman Abbas
(74) *Attorney, Agent, or Firm* — HAUPTMAN HAM, LLP

(57) ABSTRACT

Methods for improving solubility of active pharmaceutical ingredients (APIs) through co-attriting the APIs with select excipients, especially solubility enhancing excipients, and the products prepared by the methods, are disclosed. Pharmaceutical compositions containing co-attrited mixture of an API with a solubility enhancing excipient and use of the pharmaceutical compositions for treatment of diseases or disorders are also disclosed.

20 Claims, 1 Drawing Sheet

METHODS OF IMPROVING PHARMACEUTICAL SUBSTANCE SOLUBILIZATION AND PRODUCTS THEREOF

CROSS-REFERENCE TO RELATED APPLICATIONS

This application is the U.S. National Phase of International Patent Application No. PCT/US2020/027023, filed on Apr. 7, 2020, which claims priority under 35 U.S.C. § 119(e) to U.S. Provisional Application Ser. No. 62/830,740, filed on Apr. 8, 2019, the disclosures of which are incorporated herein by reference in their entirety.

FIELD OF THE INVENTION

The present invention relates to methods of improving solubility and bioavailability of active pharmaceutical ingredients (APIs) and pharmaceutical compositions containing such APIs.

BACKGROUND OF THE INVENTION

One of the most challenging problems of the pharmaceutical industry is the improvement on the solubilization and thus bioavailability of the poorly soluble drugs. The vast majority of the newly developing drugs as well as significant portion of the current medical drugs are considered poorly soluble drugs. Drug molecules can be generally categorized into four classes by the Biopharmaceutics Classification System (BCS) based on their solubility and permeability: Class I (high permeability, high solubility), Class II (high permeability, low solubility), Class III (low permeability, high solubility), and Class IV (low permeability, low solubility). The poorly soluble Class II and Class IV drug molecules constitute majority of the new drug candidates. See, e.g., World Health Organization, *WHO Technical Report Series*, 2006, No. 937, Annex 8, pp. 392-394; Amidon G L, et al., *Pharmaceutics Research*, 1995, 12:413-420.

The lack of adequate solubility puts substantial limitations on the drug molecules bioavailability, thus reducing the drug effectiveness or preventing the drug molecules' medical effects from being fully realized with safe dosages. These issues pose serious problems on the high demand medicines, such as those for antitumor drugs, cancer drugs, cardiovascular drugs, antiviral drugs, antifungal drugs, and some of the antibacterial drugs, to name a few. The poor solubility affects not only the drugs administered by enteral and gastrointestinal routes, but also the parenteral administered drugs.

There are many strategies or combinations of strategies that have been developed or explored for improving the drug solubilization. For instance, reducing the drug API (active pharmaceutical ingredient) particle sizes by micronization would improve solubility, but only to some limited extent. Incorporating the drug molecules inside a cage molecule, such as cyclodextrin, is another approach, but this approach can only be limited to very few molecules with proper size and conformations. Various excipients (mostly polymeric vehicles), surfactants (either polymers or small molecules), and lipids, have also been used as carrier to enhance the API drug molecule solubility.

Nanonization of the API drugs is currently a widely studied approach. Traditionally, sub-micron or nano drug particles can be produced by extensive, exhaustive, and time-consuming milling and grinding techniques, including high pressure homogenizations as well. Currently, the more adopted approach of nanonization is to dissolve the API into solution with proper solvents and then precipitate or emulsify the drug molecules into nano particles while stabilized by the presence of stabilizing excipients. This way, a nano particle drug dispersion is generated. Most commonly, the nano dispersion is then spray dried or freeze-dried into solids for downstream dosage forms. This technique has some drawbacks, such as a high cost of preparation, presence of residual solvents, and the limited choice of solvents used for dissolving the API molecules and excipients.

Another widely investigated approach is the hot melt extrusion (HME) which can be used to produce the solid dispersions directly. In this case, the API drug and the proper excipients are hot melted inside the hot melt extruder by the externally supplied heat, which then after cooling would form a glass solid solution (solid dispersion) or sometimes a eutectic mixture, which is then milled into solid particulates for downstream dose forms preparations. In this case, the API drug is usually transformed into a form of amorphous state for improved solubility. There are a few drawbacks of this approach. First, it cannot be applied to the heat-sensitive drugs which will cause drug degradations, especially for the high melting point drugs as well as the heat-sensitive biopharmaceuticals. Secondly, it would put a stringent equipment and operational requirement on the hot melt extruder machinery, which may not be practical for some high melting point drugs. Thirdly, the amorphous solid drug (such as stabilized by the co-melted polymeric excipients in the glassy state) is a thermodynamically unstable system, albeit having high solubility enhancement at limited time durations, which would easily re-crystallize and cause reduced solubility and stability issues with time. For instance, this typically displays a distinctive solubilization profile, so called "the Spring and Parachute" effect.

Therefore, new methods to improve solubility and bioavailability of drug substances while retaining their bioactivity and other desirable properties at the molecular level are needed.

SUMMARY OF THE INVENTION

The present invention fulfills the foregoing need by providing a method to increase solubility and bioavailability of drug substances through co-attriting active pharmaceutical ingredients (APIs) with a solubility enhancing excipient, among others, under mild conditions, which largely preserves the integrity and other properties of APIs.

In one aspect, the present invention provides a method of increasing solubility of an active pharmaceutical ingredient (API), comprising co-attriting a dry or substantially dry mixture of the API and a solubility-enhancing excipient with a kneading or extrusion device at a temperature below the melting point of the API, and applying an attrition force sufficient to increase the API solubility.

In another aspect, the present invention provides a pharmaceutical composition or dosage form comprising an API processed using a method according to any embodiment disclosed herein.

In another aspect, the present invention provides a pharmaceutical composition comprising an extruded or kneaded mixture of an active pharmaceutical ingredient (API) with a solubility enhancing excipient.

In another aspect, the present invention provides a method of treating a disease or disorder, comprising administering to a subject in need thereof a therapeutically effective amount of a pharmaceutical composition according to any embodiment disclosed herein.

In another aspect, the present invention provides a co-attrition mixture of an active pharmaceutical ingredient with a solubility enhancing excipient, which mixture preferably is made by a method of extruding or kneading as disclosed herein.

In another aspect, the present invention relates to use of a co-attrition mixture of an API with a solubility enhancing excipient in the manufacture of a medicament for treatment of a disease or disorder. The API, co-attrition mixture and preparation methods thereof, solubility enhancing excipient, and disease or disorder are all as substantially disclosed herein.

The present invention also includes any of the medicine products and pharmaceutical dosage forms, employing the preparation processes comprising the present invented co-attriting method.

Thus, the present invention provides a pharmaceutical composition of enhanced solubility, bioavailability, and preservation of bioactivity, comprising an extruded or kneaded mixture of an API of poorly soluble drug substance or heat-sensitive drug substance and compatible excipients, wherein the API molecule remains crystalline or partial crystalline, which has neither been changed by hot melting at or above its melting point nor changed by dissolution in the solvent for nanonization and redispersion/spray drying purpose.

One particular advantage of the present invention for processing the surface-functionalized drug particles would be that it is ideally suitable for the heat-sensitive poorly soluble drugs wherein the drug molecules would thermally degrade at temperatures of the drug melting points if otherwise processed by the conventional hot melt extrusions (HME). The present invention would also be a valuable means to impart a surface-functional layer or protective layer/encapsulations for the heat-sensitive biopharmaceuticals, peptide/protein drugs for oral or targeted delivery.

These and other aspects and advantages of the present invention will become more apparent in view of the following detailed description, drawings, and claims.

DETAILED DESCRIPTION OF THE INVENTION

Figure 1:
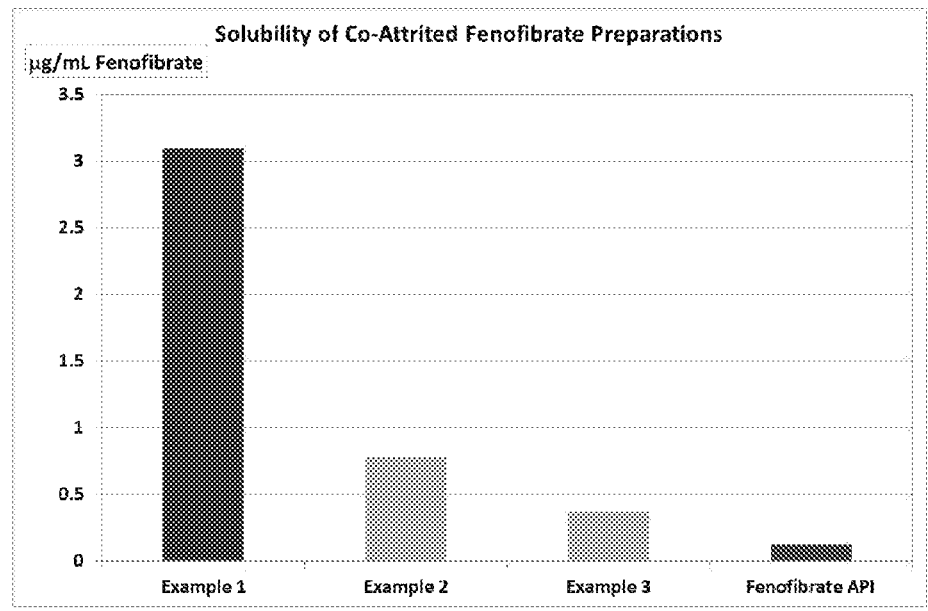
FIG. 1 illustrates the effect of co-attrition on the solubility of the Fenofibrate API.

In the present invention, we have discovered that kneading the substantially dry mixtures of the API drug crystals and the properly chosen polymeric excipients under substantially elevated torque and shear force without externally added heat, can deliver a solid or solid-like drug dispersion which exhibits substantially improved drug solubilization enhancement. Unlike the hot melt extrusion (HME) based solid amorphous dispersions, this invented process is preferably or predominantly, carried out at temperatures that are substantially below the melting point of the API drug particles or crystals, thus avoiding heat degradation of the API drug molecules. Additionally, unlike the hot melt extrusion (HME) method, the present invention, without hot-melting the API drugs, does not intend to cause any significant transformation of the API drug crystals into the amorphous solid state thus avoiding the thermodynamic instability of the amorphous drugs often encountered by the hot melt extrusion process. The present invention can be applied to a broad range of API drug molecules which also include the heat sensitive drugs and biopharmaceutical drugs.

In one aspect, the present invention provides a method of increasing solubility of an active pharmaceutical ingredient (API), comprising co-attriting a dry or substantially dry mixture of the API and a solubility-enhancing excipient with a kneading or extrusion device at a temperature below the melting point of the API, and applying an attrition force sufficient to increase the API solubility.

In one embodiment, the solubility of API is increased by at least 10% as compared with the API in a pure form, in some embodiments preferably by at least 20%, in some embodiments preferably by at least 30%, in some embodiments preferably by at least 50%, in some embodiments preferably by at least 75%, in some embodiments preferably by at least 100%, in some embodiments preferably by at least 125%, and in some embodiments preferably by at least 150% or higher.

In some embodiments of this aspect, the co-attriting is carried out by a co-attrition device selected from the group consisting of kneaders, kneading mixers, kneading extruders, extruders, and a modified hot melt extruder with a substantially augmented kneading/mixing action where no external heating is added and the API is not hot melted.

In some embodiments of this aspect, the co-attrition device is a co-rotating twin screw kneader or extruder, or an equivalent thereof, optionally with indirect or direct cooling.

In some embodiments of this aspect, the peak co-attrition torque force of the co-attrition is at least 10 N.m, in some embodiments preferably at least 15 N.m, in some embodiments preferably at least 20 N.m, in some embodiments preferably at least 30 N.m, in some embodiments preferably at least 40 N.m, in some embodiments preferably at least 50 N.m, in some embodiments preferably at least 60 N.m, and in some embodiments preferably at least 70 N.m.

In some embodiments of this aspect, the API is a BCS Class II or Class IV poorly soluble drug substance.

In some embodiments of this aspect, the API is a heat-sensitive drug molecule.

In some embodiments of this aspect, the heat-sensitive drug substance would thermally degrade at its hot melting temperature if processed with a conventional hot melt extruder.

In some embodiments of this aspect, the API is a drug molecule with a high melting temperature that could not be reached by a conventional hot melt extruder device.

In some embodiments of this aspect, the co-attrition mixture after the co-attrition process forms a solid or semi-solid dispersion comprising crystallites or partially crystalline API particles of the API.

In some embodiments of this aspect, the API is a heat-sensitive biopharmaceutical or a peptide and protein drug substance, wherein a protective layer or target chemical surface can be imparted onto the API by the co-attrition process.

In some embodiments of this aspect, the API content in the co-attrition mixture ranges from 5% to 95% by weight.

In some embodiments, the API content is in the range of 10% to 90% by weight, 20% to 80%, 30% to 70%, or 40% to 60%.

In some embodiments, the API content is in the range of 5% to 15% by weight, 15% to 25% by weight, 25% to 35% by weight, 35% to 45% by weight, 45% to 55% by weight, 55% to 65% by weight, 65% to 75%, or 75% to 85%, or 85% to 95% by weight.

In some embodiments of this aspect, the substantially dry co-attrition mixture has a moisture content less than 50%, less than 40%, or preferably less than 30% by weight, sometimes more preferably less than 20%, and sometimes more preferably less than 10%.

In some embodiments of this aspect, the solubility enhancing excipient of the co-attrition mixture is selected from the group consisting of: polyvinylpyrrolidones (Povidones), polyvinylpyrrolidone derivatives or co-polymers (Copovidones), Soluplus (polyvinyl caprolactam-polyvinyl acetate-polyethylene glycol graft co-polymer), Crospovidones, polyethyleneglycols (PEG), PEG ether and ester derivatives or co-polymers, Poloxamers (polyethylene-propyleneglycols), carboxymethyl cellulose and salts (CMC), cross-linked CMCs (Croscarmellose), HPMCAS (Hypromellose acetate succinates), HPMC (hydroxypropyl methyl cellulose), hydroxyethyl cellulose, hydroxypropyl cellulose, ethyl cellulose, methyl cellulose, beta-cyclodextrins, hydroxypropyl beta-cyclodextrins, polyethyleneoxide polymers, polyvinyl alcohols, colloidal microcrystalline cellulose/carboxymethylcellulose, microcrystalline cellulose, HPMCP (hydroxypropylmethyl cellulose phthalates), polyethylene glycol-polyvinyl alcohol co-polymers, acrylic and methacrylic polymers or co-polymers and derivatives, Cholestyramine resins, Polacrilex resins, sodium polystyrene sulfonates and co-polymers, Polacrilin potassium, starches and modified starch derivatives, hydroxypropyl pea starch, maltodextrins, alginates, pectins, carregeenans, Xanthan gum, guar gums, proteins, sugars, sugar alcohols (such as mannitol, sorbitol, xylitol), heparin, gelatins, chitosan, lipids, phospholipids, lecithin, phosphatidylcholine, and combinations thereof.

In some embodiments of this aspect, the solubility enhancing and stabilization excipient is selected from the group consisting of co-processed microcrystalline cellulose/carboxymethyl cellulose, povidones, poloxamers, Soluplus, HPMC, and combinations thereof.

In some embodiments of this aspect, the co-attrition mixture further comprises an attrition aid and/or dispersing agent selected from the group consisting of organic and inorganic particles, water-soluble salts, and water-insoluble salts.

In some embodiments of this aspect, the attrition aid or dispersing agent is selected from the group consisting of calcium carbonates, clays, calcium phosphates, calcium citrate, calcium silicates, silica, TiO2, alumina, microcrystalline cellulose, microcrystalline cellulose co-processed or blended with other excipients, powder cellulose, cellulose acetates, starches, chitin and chitosan, talc, micronized or colloidal metals (such as iron particles, silver particles, zinc particles, and gold particles), calcium chloride, calcium lactate, sodium chloride, potassium chloride, inorganic or organic ammonium salts, and combinations thereof.

In some embodiments of this aspect, the co-attrition mixture further comprises an auxiliary pharmaceutical ingredient.

In some embodiments of this aspect, the auxiliary pharmaceutical ingredient is selected from the group consisting of flavoring agents, coloring agents, pigments, sweeteners, taste-masking agents, penetrants, stabilizers, emulsifiers, surfactants, defoamers, lubricants, glidants, enzyme barriers or inhibitors (for protein and peptide drug protections), binders, disintegrants, and combinations thereof.

In some embodiments of this aspect, the method is combined with an upstream or downstream pharmaceutical processing method, and/or a pharmaceutical dosage form manufacturing process.

In another aspect, the present invention provides a pharmaceutical composition or dosage form comprising an API processed using a method according to any embodiment disclosed herein.

In one embodiment of this aspect, the pharmaceutical composition or dosage form is selected from the group consisting of antitumor drugs, anticancer drugs, antiviral drugs, antibacterial drugs, antifungal drugs, allergy drugs, cardiovascular drugs, anti-hypertension drugs, dermatology drugs, anti-protozoa drugs, anti-diabetes drugs, internal medicine drugs, nerve system drugs, mental health drugs, anti-seizure drugs, anti-epilepsy drugs, anti-depression drugs, pain relief drugs, flu relief drugs, pulmonary system drugs, respiratory system drugs, metabolism drugs, anti-attention disorder drugs, pediatric drugs, geriatric drugs, anti-aging drugs, anti-obesity drugs, cholesterol lowering drugs, anti-arthritis drugs, reproductive medicines, urinary system drugs, women's health drugs, hematology drugs, gastroenterology drugs, chemotherapy drugs, radiation therapy drugs, hormone therapy drugs, immunization drugs, anti-Aids, anti-inflammatory drugs, protein and peptide drugs, nucleotides, anesthetic drugs, psychotropic drugs, abuse prevention drugs, and organ transplant anti-rejection drugs.

In one embodiment of this aspect, the pharmaceutical composition or dosage form is selected from the group consisting of: anticancer drugs (e.g., Nilotinib, Paclitaxel, Cladribine, Altretamine, etc.); hormone drugs (e.g., Danazol, Spironolactone, Fulvestrant, etc.); anesthetic drugs, psychotropic drugs, abuse prevention drugs (e.g., Alprazolam, Oxazepam, Carbamazepine, Aripiprazole, etc.); antiviral drugs (e.g., Nevirapine, Efavirenz, Lopinavir, Ritonavir, etc.); antifungal drugs (e.g., Griseofulvin, Posaconazole, Miconazole); antibacterial drugs (e.g., Rifampicin, Sulfamethoxazole, Cefpodoxime Proxetil, etc.); protein drugs (e.g., Leuprorelin, Liraglutide, Deoxyribonuclease, Superoxide dismutase, etc.); nucleotides (e.g., Fomivirsen, Pegaptanib, Mipomersen, etc.).

In one embodiment of this aspect, the pharmaceutical composition or dosage form is a veterinary or animal drug product for birds, mammals, reptiles, fish, or crustaceous species.

In one embodiment of this aspect, the pharmaceutical composition or dosage form is a herbal medicine, Chinese medicine, or Tibetan medicine application.

In another aspect, the present invention provides a pharmaceutical composition comprising an extruded or kneaded mixture of an active pharmaceutical ingredient (API) with a solubility enhancing excipient.

In some embodiments of this aspect, the API is a poorly soluble drug substance and/or heat-sensitive drug substance.

In some embodiments of this aspect, the API in the extruded or kneaded mixture possesses enhanced solubility and/or bioavailability and maintains bioactivity.

In some embodiments of this aspect, the API molecule remains crystalline or partially crystalline, which has neither been changed by hot melting at or above its melting point nor changed by dissolution in the solvent for nanonization and redispersion/spray drying purpose.

In some embodiments of this aspect, the mixture of API and the solubility enhancing excipient is made by a method according to any of the embodiments disclosed herein.

In another aspect, the present invention provides a method of treating a disease or disorder, comprising administering to a subject in need thereof a therapeutically effective amount of a pharmaceutical composition according to any embodiment disclosed herein.

In some embodiments of this aspect, the disease or disorder is selected from the group consisting of cancers, tumors, viral infections, bacterial infections, fungal infections, allergies, cardiovascular diseases, hypertension, dermatological disease, parasitic diseases or conditions, metabolism diseases or conditions, central nervous system diseases or conditions, seizures, epilepsy, depression, pain, pulmonary diseases or conditions, respiratory disease or conditions, age-related diseases or disorders, obesity, hyperglycemia, high cholesterol, arthritis, reproductive disorders, urinary diseases or disorders, gastroenterology diseases or disorders, chemotherapy drugs, hormone disorders, inflammations, psychotropic disorders, and autoimmune diseases or disorder.

In another aspect, the present invention provides a co-attrition mixture of an active pharmaceutical ingredient with a solubility enhancing excipient, which mixture preferably is made by a method of extruding or kneading as disclosed herein.

In some embodiments of this aspect, the solubility enhancing excipient of the co-attrition mixture is selected from the group consisting of: polyvinylpyrrolidones (Povidones), polyvinylpyrrolidone derivatives or co-polymers (Copovidones), Soluplus (polyvinyl caprolactam-polyvinyl acetate-polyethylene glycol graft co-polymer), Crospovidones, polyethyleneglycols (PEG), PEG ether and ester derivatives or co-polymers, Poloxamers (polyethylene-propyleneglycols), carboxymethyl cellulose and salts (CMC), cross-linked CMCs (Croscarmellose), HPMCAS (Hypromellose acetate succinates), HPMC (hydroxypropyl methyl cellulose), hydroxyethyl cellulose, hydroxypropyl cellulose, ethyl cellulose, methyl cellulose, beta-cyclodextrins, hydroxypropyl beta-cyclodextrins, polyethyleneoxide polymers, polyvinyl alcohols, colloidal microcrystalline cellulose/carboxymethylcellulose, microcrystalline cellulose, HPMCP (hydroxypropylmethyl cellulose phthalates), polyethylene glycol-polyvinyl alcohol co-polymers, acrylic and methacrylic polymers or co-polymers and derivatives, Cholestyramine resins, Polacrilex resins, sodium polystyrene sulfonates and co-polymers, Polacrilin potassium, starches and modified starch derivatives, hydroxypropyl pea starch, maltodextrins, alginates, pectins, carregeenans, Xanthan gum, guar gums, proteins, sugars, sugar alcohols (such as mannitol, sorbitol, xylitol), heparin, gelatins, chitosan, lipids, phospholipids, lecithin, phosphatidylcholine, and combinations thereof.

In some embodiments of this aspect, the solubility enhancing and stabilization excipient is selected from the group consisting of co-processed microcrystalline cellulose/carboxymethyl cellulose, povidones, poloxamers, Soluplus, HPMC, and combinations thereof.

In some embodiments of this aspect, the co-attrition mixture further comprises an attrition aid and/or dispersing agent selected from the group consisting of organic and inorganic particles, water-soluble salts, and water-insoluble salts.

In some embodiments of this aspect, the attrition aid or dispersing agent is selected from the group consisting of calcium carbonates, clays, calcium phosphates, calcium citrate, calcium silicates, silica, TiO2, alumina, microcrystalline cellulose, microcrystalline cellulose co-processed or blended with other excipients, powder cellulose, cellulose acetates, starches, chitin and chitosan, talc, micronized or colloidal metals (such as iron particles, silver particles, zinc particles, and gold particles), calcium chloride, calcium lactate, sodium chloride, potassium chloride, inorganic or organic ammonium salts, and combinations thereof.

In some embodiments of this aspect, the co-attrition mixture further comprises an auxiliary pharmaceutical ingredient.

In some embodiments of this aspect, the auxiliary pharmaceutical ingredient is selected from the group consisting of flavoring agents, coloring agents, pigments, sweeteners, taste-masking agents, penetrants, stabilizers, emulsifiers, surfactants, defoamers, lubricants, glidants, enzyme barriers or inhibitors (for protein and peptide drug protections), binders, disintegrants, and combinations thereof.

In some embodiments of this aspect, the API content in the co-attrition mixture ranges from 5% to 95% by weight.

In some embodiments, the API content is in the range of 10% to 90% by weight, 20% to 80%, 30% to 70%, or 40% to 60%.

In some embodiments, the API content is in the range of 5% to 15% by weight, 15% to 25% by weight, 25% to 35% by weight, 35% to 45% by weight, 45% to 55% by weight, 55% to 65% by weight, 65% to 75%, or 75% to 85%, or 85% to 95% by weight.

In another aspect, the present invention relates to use of a co-attrition mixture of an API with a solubility enhancing excipient in the manufacture of a medicament for treatment of a disease or disorder. The API, co-attrition mixture and preparation methods thereof, solubility enhancing excipient, and disease or disorder are all as substantially disclosed herein.

The co-attrition is carried out on dry mixtures or the substantially dry mixtures comprising API drug particles and proper excipients which are chemically compatible with these API drug particles. The co-attrition process is the key factor in improving the drug solubility substantially wherein the co-attrited drug particles would also be stable in the solution for extended time sufficient to deliver the drug effect.

It is critical to choose a proper co-attriting device which can deliver sufficient mechanical shearing and/or compacting force. For example, a co-rotating twin screw kneader or extruder, operating at high torque force can be used. Another example would be a conventional hot melt extruder whereas no heat is externally supplied for hot melting the API drugs and the kneading/mixing action is substantially augmented, or modified beyond the usual operating range of the conventional pharmaceutical hot-melt extrusions. The co-attriting device can also be carried out by other dry attriting mechanical devices such as a high pressure press (either roll or flat plate) or a supercalendaring device when properly reconfigured or modified.

The co-attriting device is preferably a kneader, a kneading mixer device, a kneading extruder device, or an extruder device. Preferably, the co-attriting or kneading device can deliver a peak torque force at least 30 N.m, and more preferably at least a peak torque of 50 N.m. One particular example of the co-attriting device is a co-rotating twin screw kneader or extruder. Furthermore, the co-attriting device can also be modified from a conventional hot melt extruder (HME) whereas the heat is not externally supplied and/or the melting point of API drug crystal is not exceeded (no-melting), and whereas the mixing and kneading zone is substantially augmented to surpass the conventional hot melt extruder torque and force transfer levels usually used for producing the pharmaceutical amorphous solid dispersions.

Any kneaders, extruders, press or other mechanical attrition devices are included. Without being limited to it, one particular example is a KRC Kneader as marketed by Kurimoto Ltd, or the equivalents. Other non-limiting examples include extruders and hot melt extruders (operating without melting API drug) such as from the following types or manufacturers: Leistritz, Milacron, Xtrutech, Coperion, Gabler, Baker Perkins, Davis-Standard, Thermo Fisher, and any other local types, extensions, and modifications from local manufacturers.

In one embodiment, the co-attriting kneading or extrusion devices can deliver a peak torque force at least 30 N.m, and more preferably at least a peak torque of 50 N.m. In another embodiment the peak torque force of at least 80 N.m is applied. In yet another embodiment, a peak torque force of at least 100 N.m is applied.

The co-attriting dry mixtures of API drug and excipients can be any dry materials, dry powders or particulates. The dry solids content can also be from 50% solids to 100% solids, preferably from 60% solids to 100% solids, more preferably from 70% to 100% solids, whereas the rest material in the co-attrition mixture being water moisture, aqueous solution/dispersions of certain excipients, solvents or ammonia solution/dispersions, or liquid state excipients. In one embodiment, water shower or mists is used. In another embodiment, ammonia or aqueous ammonia is used. Other non-limiting liquid state excipient examples include glycols, liquid state poly-glycols (such as polyethylene glycols, polypropylene glycols, or mixtures and co-polymers), various liquid state glycol ethers or esters, glycerol, oils and liquid lipids.

The co-attrition is conducted without the melting of API drug. Preferably, the co-attrition is carried out with proper cooling. The cooling of the co-attrition can be done either indirectly or directly. Non-limiting examples of indirect cooling include strategies achieved through the cooling jacket, or by cooling of the mixer blades, axels, mixing paddles, or external kneader/extruder chambers. Any common cooling media can be used for the indirect cooling, including water, chilled water, chilled salt water, glycols, water-glycols mixtures, ammonia, etc. In direct cooling, the cooling media can be in direct contact with the co-attrition mixture inside the kneader/extruder chamber. For the direct cooling, non-limiting examples of cooling media include ammonia, dry ice, ammonium salts, ice, ice-water, chilled water or solvents, chilled salt water, or liquefied gas such as liquid nitrogen. In one embodiment, the direct cooling media include dry ice, aqueous or liquid ammonia, ammonium bicarbonate, and ammonium carbonate, which would be easily evaporated after the co-attrition without leaving any significant residues in the mixture, especially after drying. In one variation of the direct cooling, a frozen mixture of API drug and excipients may be co-attrited.

In one embodiment, one or more of the co-attriting excipients may be melted by the heat generated by the co-attrition actions whereas the API drug is not melted.

The co-attriting device can either be operated batch-wise or be operated continuously. The operation can also be carried out in series of a few kneaders or extruders, which are arranged in various combinations of sequential orders or parallel lines. The co-attriting operation can be conducted with partial or total returns of the processing streams. As stated above, cooling is preferably applied during the co-attrition process. Further, after the co-attrition stage outlet, or at the outlets of the interim stages or passes, the co-attrited or partially co-attrited API/excipients mixture can also optionally be cooled by any means including but not limited to cooling rolls, cooling mixers, cooling extruders, cooling screw conveyers, etc., which can then go through further downstream milling and any of the pharmaceutical dosage form preparations.

When applicable, method of the present invention can optionally be combined with any other conventional processing methods including, but not limited to, high pressure homogenization, emulsification, centrifugation, spray drying, lyophilization, any other drying, and conventional hot melt extrusion, etc. For example, the co-attrition of the present invention may be combined with conventional hot melt extrusion to further improve API/excipients dispersion uniformity and solubility. More interestingly, if there are two or more APIs in the mixture wherein one of the API melting temperature exceeds the conventional hot melt extruder design temperature range, the present co-attrition may then optionally be combined with the conventional hot melt extrusion to deliver the improved solubilization.

In the dry or substantially dry co-attrition mixture, the API drug amount ranges from 10% to 95% on dry weight basis, preferably from 10% to 80% dry weight. In one embodiment, the API drug ranges from 20% to 80% on dry weight basis. The rest dry mass portions are excipient or excipients. For the substantially dry mixtures, the water applied to the mixture may be less than 50%, preferably less than 40%, more preferably less than 30%, on the total weight basis. In one embodiment, the water applied to the mixture may be from 5% to 15% on total weight basis. In the dry or substantially dry co-attrition mixture, liquid state excipients (other than water) would be counted as the dry excipients as stated above.

During the co-attrition stage or stages, the moisture content of the substantially dry API/excipients mixture may decrease, by venting or by natural evaporation in air. In one embodiment, the substantially dry mixture becomes dry after the co-attrition stage or stages. In another embodiment, the substantially dry mixture after co-attrition may optionally be further dried in-line or off-line, by any drying methods. Non-limiting examples of the drying methods include through-air drying, fluidized bed drying, Infra-red drying, microwave drying, inductive drying, open air drying, oven drying, flash drying, etc., followed by optional post-milling and any downstream pharmaceutical dosage form preparations. The post-milling methods include non-limiting examples such as dry milling, wet milling, ball milling, jet milling, air-jet milling, cryogenic milling, etc.

The physical shape of the API/excipients mixture after the co-attrition can be any forms, such as noodles, pellets, granules, particles, powders, needles, chunks, ribbons, strings, loafs, slices, and any other geometrical forms, depending on the co-attriting device barrel geometry and the device exit end-plate geometry and openings shape and dimensions as well as the extrudant mixture physical and material properties. The shapes, compaction, and flow properties may also be affected by the post-milling strategies.

It is believed, without being bound to it, that the present invention achieves improved drug solubilization by the following combined mechanisms which will take place inside the co-attrition devices: (1) the high intensity kneading and attrition actions reduce the API drug particles sizes substantially to the level of micronized or submicron particles; (2) the properly select excipients or at least one of the select excipients would yield, deform, and flow under the extreme mechanical force and would disperse, coat, and bind to these API drug particle surfaces. It is most important that the intense kneading actions, which would be facilitated by the excipients' proper physicochemical properties as well as the properly adjusted dry or substantially dry solids content (for efficient force transfer), would force the select excipient molecules to bond to these API drug particles; (3) these surface-functionalized drug particles would substantially improve the water solubility of the poorly soluble drugs, which would also, optionally with other auxiliary excipients, further stabilize the supersaturated drug solutions over time; (4) these surface-functionalized drug particles could also be properly constructed with proper excipients to deliver enhanced target drug absorption, permeation, or bioavailability.

The co-attriting excipients act to function as API drug carriers, penetrants, solubilizers, stabilizers, emulsifiers, surfactants, wherein at least one of the excipients would soften, flow, or melt (or dissolve in the applied water in the case of the substantially dry mixture) during the attrition, which would coat or attach to the co-attrited API drug particles. In this way, the API drug water solubility would increase and would be stabilized. At least one of the co-attriting excipients shall readily dissolve or disperse into the water solutions. In one embodiment, the excipient may be an amphoteric polymer with both hydrophilic portions (affinity to water solutions) and hydrophobic domains (affinity to the hydrophobic poorly soluble API drug molecules). In other embodiment, some of the excipients may be added to function as stabilizers to sustain the augmented API solubility over the effective time period. Often times, a combination of a few excipients are used to achieve this purpose, in which case at least one of the excipients would flow and attach to the API drug particles in the co-attriting API/excipients dry mixture, or in which case at least one of the excipients would dissolve in the applied water and coat the API drug particles in the co-attriting substantially dry API/excipients mixture.

The excipients that are co-attrited with the API drug particles can be selected from any polymeric, oligomeric, or chemical excipients which can deform, yield, plasticize, soften, flow, or disperse under the intense kneading and extrusion actions and/or other mechanical forces, and which can effectively attach or bind with the co-attriting API drug particle surfaces under the co-attriting actions, while in the meantime these excipients shall readily solubilize or disperse into the water solutions. These excipients include the pharmaceutical carriers, solubilizers, stabilizers, surfactants, and emulsifiers which have been conventionally used as API drug carriers, and micro or nano drug carriers, especially those which have been employed by the spray dried nano dispersion/emulsions systems and those employed by the pharmaceutical solid amorphous dispersion/solution systems such as those applied in the hot melt extrusion process.

Examples of these excipients include, but not limited to, PVP (Povidones), PVP derivatives (Copovidones), Soluplus (polyvinyl caprolactam-polyvinyl acetate-polyethylene glycol graft co-polymer), PEGs, PEG derivatives and co-polymers, polyethylene-propyleneglycols (Poloxamers), various cellulose ether or ester derivatives, HPMCAS (Hypromellose acetate succinates), HPMC (hydroxypropyl methyl cellulose), beta-cyclodextrins and derivatives, polyethyleneoxide polymers, polyvinyl alcohols, colloidal microcrystalline cellulose/carboxymethylcellulose, HPMCP (hydroxypropylmethyl cellulose phthalates), polyethylene glycol-polyvinyl alcohol co-polymers, acrylic and methacrylic co-polymers, polystyrene sulfonates and co-polymers, starch and modified starch derivatives, sugars and sugar alcohols, various hydrocolloids and lipids, etc.

Some more specific non-limiting examples of these excipients are listed below: Povidones of various grades and molecular weights, such as Plasdone K29/32, Kollidon K30, K90; PVP derivatives (Copovidones, such as Plasdone S-630, Kollidon VA64), Soluplus (polyvinyl caprolactam-polyvinyl acetate-polyethylene glycol graft co-polymer), crospovidone, PEG, PEG ether and ester derivatives or co-polymers, Poloxamers of all types (such as Poloxamer 188, and 407), various cellulose derivatives, carmellose, croscarmellose, hypromellose, HPMCAS (hypromellose acetate succinates), HPMC (hydroxypropyl methyl cellulose), beta-cyclodextrins (such as KLEPTOSE), hydroxypropyl beta-cyclodextrins (such as KLEPTOSE HPB, HP), polyethyleneoxide polymers (such as POLYOX), polyvinyl alcohols, colloidal microcrystalline cellulose/carboxymethylcellulose (such as Vivapur, Avicel or similar colloidal grades), HPMCP (hydroxypropylmethyl cellulose phthalates), polyethylene glycol-polyvinyl alcohol co-polymers, acrylic and methacrylic polymers and co-polymers and derivatives (such as EUDRAGIT of all types, Kollicoat MAE and other Kollicoat types, Carbopol and Pemulen of all types), Cholestyramine resins (such as DUOLITE A143), Polacrilex resins (such as AMBERLITE IRP 64), sodium polystyrene sulfonates (such as AMBERLITE IRP 69), Polacrilin potassium (AMBERLITE IRP 88), starch and modified starch derivatives (such as hydroxypropyl pea starch), maltodextrins, alginates, pectins, carregeenans, Xanthan gum, sugars, sugar alcohols (such as mannitol, sorbitol, xylitol), heparin, gelatins, chitosan, lipids, phospholipids, lecithin, phosphatidylcholine, etc.

Co-attriting excipients may also include agents (particles, soluble and insoluble salts) which may aid in the attriting actions.

Included are also excipients acting or partially acting as co-attrition enhancing agents or attrition aids. These attrition aids include organic or inorganic particles, powders, as well as water-soluble salts and water-insoluble salts. Non-limiting examples include: calcium carbonate, clays, calcium phosphates, calcium citrate, calcium silicates, silica, TiO2, microcrystalline cellulose, powder cellulose, starches, chitin and chitosan, PVPP, talc, alumina, micronized or colloidal metals (such as iron particles, silver particles, and gold particles), as well as calcium chloride, calcium lactate, sodium chloride, etc. A particular example is microcrystalline cellulose (MCC) binders, such as Avicel PH 101, 102, 112, 105, 301, 302, 200, and various low moisture MCC grades, as well as the equivalent or similar products from various manufacturers. Another example is the MCC co-processed products or co-blends, such as MCC/mannitol, MCC/calcium phosphates, MCC/silica or PROSOLV, to name a few.

In one embodiment, the solubility enhancing and stabilization excipients include, but are not limited to, co-processed microcrystalline cellulose/carboxymethyl cellulose, povidones, poloxamers, Soluplus, HPMC, and any combinations thereof.

Also included in the co-attrition mixtures are any other auxiliary ingredients, such as flavoring agents, coloring agents, pigments, sweeteners, and taste-masking agents, etc.

Any medicines and pharmaceutical products prepared comprising the present invented method are included. They include, but not limited to, any antitumor drugs, anticancer drugs, antiviral drugs, antibacterial drugs, antifungal drugs, allergy drugs, cardiovascular drugs, anti-hypertension drugs, dermatology drugs, anti-protozoa drugs, anti-diabetes drugs, internal medicine drugs, nerve system drugs, mental health drugs, anti-seizure drugs, anti-epilepsy drugs, anti-depression pain relief drugs, flu relief drugs, pulmonary system drugs, respiratory system drugs, metabolism drugs, anti-attention disorder drugs, pediatric drugs, geriatric drugs, anti-aging drugs, anti-obesity drugs, cholesterol lowering drugs, anti-arthritis drugs, reproductive medicine drugs, urinary system drugs, women's health drugs, hematology drugs, gastroenterology drugs, chemotherapy drugs, radiation therapy drugs, hormone therapy drugs, immunization drugs, anti-Aids, anti-inflammatory drugs, protein and peptide drugs, nucleotides, anesthetic drugs, psychotropic drugs, abuse prevention drugs, and organ transplant anti-rejection drugs, etc. Also included are the pharmaceutical products of Chinese traditional medicines, herbal medicines, and Tibetan medicines prepared comprising method of the present invention. Further, included are all the veterinary and animal medicines prepared by methods comprising the current method, including the drugs for birds, mammals, reptiles, fish and crustaceous species.

While not limiting, the drugs suitable for the present invention include anticancer drugs such as (but not limited to) Nilotinib, Paclitaxel, Cladribine, Altretamine; hormone drugs such as (but not limited to) Danazol, Spironolactone, Fulvestrant; anesthetic drugs, psychotropic drugs, abuse prevention drugs such as (but not limited to) Alprazolam, Oxazepam, Carbamazepine, Aripiprazole; antiviral drugs such as (but not limited to) Nevirapine, Efavirenz, Lopinavir, Ritonavir; antifungal drugs such as (but not limited to) Griseofulvin, Posaconazole, Miconazole; Antibacterial drug such as (but not limited to) Rifampicin, Sulfamethoxazole, Cefpodoxime Proxetil; Protein drugs such as (but not limited to) Leuprorelin, Liraglutide, Deoxyribonuclease, Superoxide dismutase; Nucleotide such as (but not limited to) Fomivirsen, Pegaptanib, Mipomersen; or the like.

All pharmaceutical dosage forms, intermediates, and constituents prepared by methods comprising the present invention method, in parts, in whole, or in partially equivalent strategies, are included. Non-limiting examples of dosage forms include tablets, micro tablets, pellets, micro pellets, coated tablets, coated pellets, capsules, micro-capsules, coated capsules, controlled release dosage forms, sustained release forms, extended release forms, fast release forms, orally disintegrating tablets, oral dispersible pellets, enteric and gastrointestinal coated dosage forms, taste masking tablets, liquid suspensions, emulsions, parenteral dosage forms such as injectable dosage forms, ointment, lotions, creams, inserts, patches, and implanted dosage forms. Included also are any dosage form preparation methods. For instance, a few non-limiting examples of the most common tableting manufacturing methods include direct compression, wet granulation, and dry granulation.

Biopharmaceuticals such as the protein and peptide drugs present different challenges. First, their multi-level macromolecular superstructures and configurations (thus activity or effectiveness) are extremely heat sensitive. The pharmaceutical dosage forms of protein and peptide drugs are mostly administered through the IV, IM, or SC routes. The co-attrition method of the present invention, through proper selection of the co-attrition excipients, can be utilized to create specific chemical surfaces or associations to the drug molecules, which would modify the drug surface hydrophobicity or impart target affinity. The oral dosage forms of protein and peptides drugs would have additional difficulties in order to overcome the gastric acid barriers, digestive enzyme or protease enzyme barriers, and the membrane transport barriers, although some special mechanisms of cell transport channels do exist. By selecting the proper co-attrition excipients and the concomitant drug particle size reduction (such as micronization and nanonization), the co-attrition method of the present invention may serve to create specific protective layers, which in combination with other protection mechanisms such as capsules, encapsulations, and coatings, would enhance the drug bioavailability and deliver improved drug effectiveness.

As used herein, the term "active pharmaceutical ingredient" (API) sometimes is used interchangeably with the terms "drug substance", "drug", "compound", "therapeutic agent", etc. It includes small molecules, either freebase, free acid, or pharmaceutically acceptable salts or solvates thereof, large molecules, such as peptides and proteins, nucleosides, nucleotides, or the like.

As used herein, the term "poorly water soluble" refers to a substance, for example API, that has less than 5 mg/mL, less than 2 mg/mL, or less than 1 mg/mL solubility in the physiological pH range at 25-30° C. For example, the solubility of an API can be determined by adding the highest dose strength in 250 mL of aqueous solutions ranging from pH 1 to 7.4 to cover GI physiological conditions. If there is less than 250 mg of API dissolved in 250 mL of solution of any pH from 1-7.4, the API is considered to be poorly water soluble.

A "pharmaceutical composition" refers to a mixture of an API or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient and thus displaying biological activity.

"Pharmaceutically acceptable salts" refer to salts of the compounds of the invention, such salts being safe and effective when used in a mammal and have corresponding biological activity.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject.

The term "solvate," as used herein, means a physical association of a compound of this invention with one or more, preferably one to three, solvent molecules, whether organic orinorganic. This physical association includes hydrogen bonding.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "treat", "treating", "treatment", or the like, refers to: (i) inhibiting the disease, disorder, or condition, i.e., arresting its development; and (ii) relieving the disease, disorder, or condition, i.e., causing regression of the disease, disorder, and/or condition.

The term "subject" or "patient" refers to a mammalian animal.

The term "mammal" or "mammalian animal" includes, but is not limited to, humans, dogs, cats, horses, pigs, cows, monkeys, rabbits and mice. The preferred mammals are humans.

As used herein, the singular forms "a", "an", and "the" include plural reference, and vice versa, unless the context clearly dictates otherwise.

All the above invention disclosures, descriptions, and embodiments examples, including any extensions, variations, modifications, and equivalent methodologies, are herein included in the present invention.

The following non-limiting examples further illustrate some aspects of the present invention.

EXAMPLES

Materials
API Drugs:

Fenofibrate (melting point 80-81 C) and Carbamazepine (melting point 189-192 C) were used as the models for the poorly soluble drugs. They were purchased from the market place.

Excipients:

All the excipients used in this study were purchased from the market place:

Kollidon K30 (manufactured by BASF) is a PVP (Povidone) product.

Kollidon V64 (manufactured by BASF) is a Copovidone product. It is a vinylpyrrolidone-vinyl acetate copolymer.

Kolliphor P188 (manufactured by BASF) is a Poloxamer (polyethyleneglycol-propyleneglycols co-polymer) product.

Compritol 888 ATO (manufactured by Gattefosse) is a glyceryl dibehenate product.

Soluplus (manufactured by BASF) is a polyvinyl caprolactam-polyvinyl acetate-polyethylene glycol graft co-polymer product.

Vivapur MCG 811 (manufactured by J. Rettenmaier) is a co-processed microcrystalline cellulose and sodium carboxymethylcellulose (MCC/CMC) product.

Vivapur PH 102 (manufactured by J. Rettenmaier) is a pharmaceutical grade microcrystalline cellulose (MCC) binder product.

The following examples illustrate the effect of solubility enhancement imparted by the present invention on some of the poorly soluble drug models. These examples are by no means limiting, and any modifications, optimizations and extensions are covered by the present invention.

Example 1 Co-Attrition of Fenofibrate, Povidone, and MCC/CMC

A mixture of 300 gram of Fenofibrate, 400 gram of Kollidon K30, and 300 gram of Vivapur MCG 811 was mixed in a Hobart Mixer while sprayed with 150 gram of DI water. The mixture was then fed into a KRC Kneader for a few passes with indirect water cooling through the Kneader jacket. The torque was maintained between 40 N.m to 150 N.m by adjusting the material feed rate. The kneader temperature was maintained below the melting point of the API (Fenofibrate), and most of the time between 22° C. to 50° C. range. After kneading, the extrudant which was substantially dry, was milled by a coffee bean grounder into powder for downstream testing or dosage form preparations.

Example 2 Co-Attrition of Fenofibrate, Copovidone, and MCC

A mixture of 500 gram of Fenofibrate, 500 gram of Kollidon VA64, and 500 gram of Vivapur PH102 was mixed in a Hobart mixer while spraying with 176 gram of DI water. The mixture was then fed into a KRC Kneader for a few passes with indirect water cooling through the Kneader jacket. The torque was maintained between 40 N.m to 150 N.m by adjusting the material feed rate. The kneader temperature was maintained below the melting point of the API (Fenofibrate), and mostly between 22° C. to 44° C. range. After kneading, the extrudant which was substantially dry, was milled by a coffee bean grounder into powder for downstream testing or dosage form preparations.

Example 3 Co-Attrition of Fenofibrate, Copovidone, and MCC

A mixture of 250 gram of Fenofibrate, 500 gram of Kollidon VA64, and 500 gram of Vivapur PH102 was mixed in a Hobart mixer while spraying with 139 gram of DI water. The mixture was then fed into a KRC Kneader for a few passes with indirect water cooling through the Kneader jacket. The torque was maintained between 40 N.m to 150 N.m by adjusting the material feed rate. The kneader temperature was maintained below the melting point of the API (Fenofibrate), and mostly between 22° C. to 44° C. range. After kneading, the extrudant which was substantially dry, was milled by a coffee bean grounder into powder for downstream testing or dosage form preparations.

Example 4 Solubility Improvement of Co-Atrrited Fenofibrate and Excipients

All the dry powder samples from Example 1-3 were milled again and pass through an 80 mesh screen. The Fenofibrate API sample was used as the control.

For solubility testing, a given weight amount of the sample was put into 100 mL DI water inside a glass container placed at a 37° C. constant temperature water bath with shaking for 3 hours. Then a given amount of the solution was taken, filtered through a 0.8 μm syringe microfilter, and tested by a UV-Vis Spectrophotometer at 286 nm wavelength. For reference, the API Fenefibrate sample was used as control.

The results as shown below indicate that the Fenofibrate solubility was significantly improved by the present invention. An improvement of Fenofibrate solubility by 185%-2285% was achieved (see Table 1 and FIG. 1).

TABLE 1

| Samples | Fenofibrate Solubility in H2O | Solubility Improvement |
|---|---|---|
| Example 1 | 3.1 μg/mL) | By 2285% |
| Example 2 | 0.78 μg/mL | By 500% |
| Example 3 | 0.37 μg/mL | By 185% |
| Fenofibrate API | 0.13 μg/mL | base |

Example 5 Fenofibrate Solubility Testing: Time Effect

In this solubility testing, the sample preparation and dissolution were carried out in a similar way as in Example 4. The solution samples were then filtered through a 0.45 μm syringe micro filter and tested by a UV-Vis spectrophotometer. The testing was measured at 15 minutes and 60 minutes dissolution time periods at 37° C., with shaking and mixing maintained during the dissolution periods.

The results are shown below. It is noted that solubilization time would have an impact on the solubility values. Nevertheless, the enhancement of Fenofibrate solubility by the present invention is again verified. An improvement by 78% to 1036% was achieved.

TABLE 2

| Samples | Fenofibrate Solubility at 15 Minutes | | Fenofibrate Solubility At 60 Minutes | |
| --- | --- | --- | --- | --- |
| Example 1 | 4.022 µg/mL | Improve by 1036% | 3.751 µg/mL | Improve by 900% |
| Example 2 | 0.771 µg/mL | Improve by 118% | 0.667 µg/mL | Improve by 78% |
| Fenofibrate API | 0.354 µg/mL | Base | 0.375 µg/mL | Base |

Example 6 Co-Attrition of Fenofibrate, Poloxamer, and MCC/CMC and Solubility Testing A mixture 1000 gram of Fenofibrate, 500 gram of Poloxamer P188, and 500 gram of Vivapur MCG811 was dry mixed with composition ratios 2:1:1. Then the dry mixture was fed into a KRC Kneader for a few passes with indirect water cooling through the kneader jacket. The torque was maintained between 54 N.m to 103 N.m by adjusting the material feed rate. The kneader temperature was maintained between 26.1° C. to 32.5° C. range. After kneading, the extrudant was milled by a coffee bean grinder into powder and pass through a 80 mesh screen for down stream solubility testing and dissolution testing.

For solubility testing, a given amount of the above powder was put into 500 mL DI water inside a glass jar container equipped with a paddle stirring at 100 rpm which is placed at a 25° C. constant temperature control bath for 120 minutes. At each time interval, a given amount of solution was sampled and tested by a UV-Vis spectrophotometer at 289 nm. For reference, the API Fenofibrate was also tested for comparisons. The solubility results, in terms of drug concentration (µg/mL), are shown below.

TABLE 3

| Time (minutes) | API Fenofibrate (µg/mL) | Invention Sample (µg/mL) | Solubility Improvement, by |
| --- | --- | --- | --- |
| 5 | 0.1669 | 2.522 | 1411% |
| 10 | 0.1669 | 2.263 | 1256% |
| 20 | 0.1767 | 2.263 | 1181% |
| 40 | 0.1473 | 2.802 | 1802% |
| 60 | 0.2062 | 2.696 | 1208% |
| 90 | 0.1866 | 3.062 | 1541% |
| 120 | 0.3339 | 3.331 | 898% |

Significant solubility concentration improvement was demonstrated by more than 898%.

Example 7 Co-Attrition of Fenofibrate, Poloxamer, and MCC/CMC and Dissolution Curve Testing An example of dissolution curve is provided here to demonstrate the Fenofibrate drug dissolution and release rate of the co-attrited Fenofibrate sample of the present invention. The co-attrited Fenofibrate:Poloxamer:MCC/CMC (2:1:1) sample was prepared in the same composition ratio and methodology as per Example 6.

A widely accepted Hanson dissolution testing instrument was used, and the testing conditions similar to the Chinese Pharmacopeia method for Fenofibrate were adopted. It was based on a paddle stirring at 100 rpm in 1000 mL media (water) for 60 minutes and tested by the UV method at 289 nm. 1% SDS was used, and the temperature was controlled at 37° C. For reference, a commercial Fenofibrate drug, Lipanthyl Supra tablet was tested. The results are shown below.

Dissolution and Release Results:

TABLE 4

| Time (min.) | Invention Sample | Reference Drug |
| --- | --- | --- |
| 0 | 0% | 0% |
| 5 | 69% | 19% |
| 10 | 88% | 49% |
| 15 | 89% | 74% |
| 30 | 95% | 95% |
| 60 | 97% | 97% |

The results demonstrate that very satisfactory drug dissolution rate and release amount was achieved on the invention sample.

Example 8 Co-Attriting of Carbamazepine, Soluplus, and Poloxamer

A mixture of 600 gram of Carbamazepine, 200 gram of Soluplus, and 200 gram of Kolliphor (Poloxamer) P188 was mixed in a Hobart Mixer. The dry mixture was then fed into a KRC Kneader and co-attrited for a few passes. During the co-attrition, the torque started from 80 N.m and reached 140 N.m in the end. The temperature rose from 30° C. to over 50° C., reaching 70° C. in the end. These extrusion temperatures were far below the melting point of Carbamazepine (189-192° C.). After the kneading/extrusion, the dry extrudant was collected for following solubility testing.

Example 9 Co-Attriting of Carbamazepine, Povidone, and MCC/CMC

A mixture of 300 gram of Carbamazepine, 400 gram of Kollidon K30, and 300 gram of Vivapur MCG 811 was mixed in a Hobart Mixer while being sprayed with 150 gram of DI water. This substantially dry mixture was then co-attrited with a KRC Kneader for several passes. During the attrition, temperature rose gradually from 22° C. to over 70° C., and then the extrusion was cooled indirectly to 45° C. by running the tap water through the kneader/extruder vessel outer jacket. These extrusion temperatures were far below the melting point of Carbamazepine (189-192° C.). The co-attrition was conducted with a torque starting from 60 N.m and reaching 180 N.m in the end. After the co-attrition, the substantially dry extrudant was collected for following solubility testing.

Example 10 Co-Attriting of Carbamazepine and Poloxamer

A mixture of 1500 gram of Carbamazepine and 500 gram of Poloxamer P188 was mixed in a Hobart Mixer. This dry mixture was co-attrited in a KRC Kneader for several passes. The extrusion temperature rose from 22 C to 34° C., and the extrudant became soft and less efficient in extrusion. After cooling water started to run through the kneader cooling jacket, the extrudant was cooled to 27.8° C. and became slightly harder. During the kneading/extrusion, the torque stayed around 80 N.m, and reached 110 N.m in the end with water (jacket) cooling and extrudant hardening. After co-attrition, the final extrudant was collected for the following solubility testing.

Example 11 Co-Attriting of Carbamazepine, Poloxamer and Surfactant

A mixture of 700 gram of Carbamazepine, 250 gram of Poloxamer P188, and 50 gram of Compritol 888 ATO was mixed in a Hobart Mixer. This dry mixture was then co-attrited in a KRC Kneader for several passes. The co-attrition temperature rose from 23.6° C. to 60° C., and reaching 86° C. in the end. These temperatures was substantially lower than the melting point of ° Carbamazepine (189-192° C.). The attrition process was quite efficient, with torque increasing quickly from 90 N.m to 140 N.m, and reaching 160 N.m at some point of time. Unlike the case of Example 10, the extrudant of this Example 11 (with the presence of Compritol 888 ATO) did not become soft. After the co-attrition, the final extrudant was collected for following testing.

Example 12 Solubility Time Profile of Co-Attrited Carbamazepine

All the final extrudant samples from Examples 8-11 were milled into powder and passed through an 80 mesh screen. Then, a given weight amount of the sample was put into 100 mL DI water container placed at a 37° C. constant temperature water bath with fixed shaking and stirring for 3 hours, while solution samples were taken for solubility testing at appropriate time intervals. At each sampling time, the solution sample was taken and filtered through a 0.45 μm syringe microfilter. The filtrate was tested by a UV-Vis Spectrophotometer at 285 nm wavelength for Carbamazepine. For reference, the API Carbamazepine sample was used as control.

The results as shown in Table 5 below indicate that in the cases of Example 8 and Example 9, the co-attrited Carbamazepine solubility was significantly improved. In the case of Example 10 and Example 11, the solubility improvement was modest, despite that these samples seemed to disperse readily and fast in water.

TABLE 5

| Time Intervals (min) | Example 8 Solubility (mg/mL) | Example 9 Solubility (mg/mL) | Example 10 Solubility (mg/mL) | Example 11 Solubility (mg/mL) | Carbamazepine API Solubility (mg/mL) |
|---|---|---|---|---|---|
| 5 | 0.625 | 0.541 | 0.493 | not sampled | 0.404 |
| 10 | 0.688 | not sampled | 0.497 | not sampled | 0.402 |
| 15 | 0.675 | 0.587 | 0.429 | 0.434 | 0.401 |
| 30 | 0.810 | 0.550 | 0.436 | 0.439 | not sampled |
| 60 | 0.790 | 0.391 | 0.395 | 0.376 | 0.320 |
| 90 | not sampled | 0.412 | 0.348 | 0.344 | 0.316 |
| 120 | 0.812 | not sampled | 0.316 | 0.355 | 0.303 |
| 180 | 0.815 | 0.372 | 0.324 | 0.348 | 0.288 |

Figure 2:
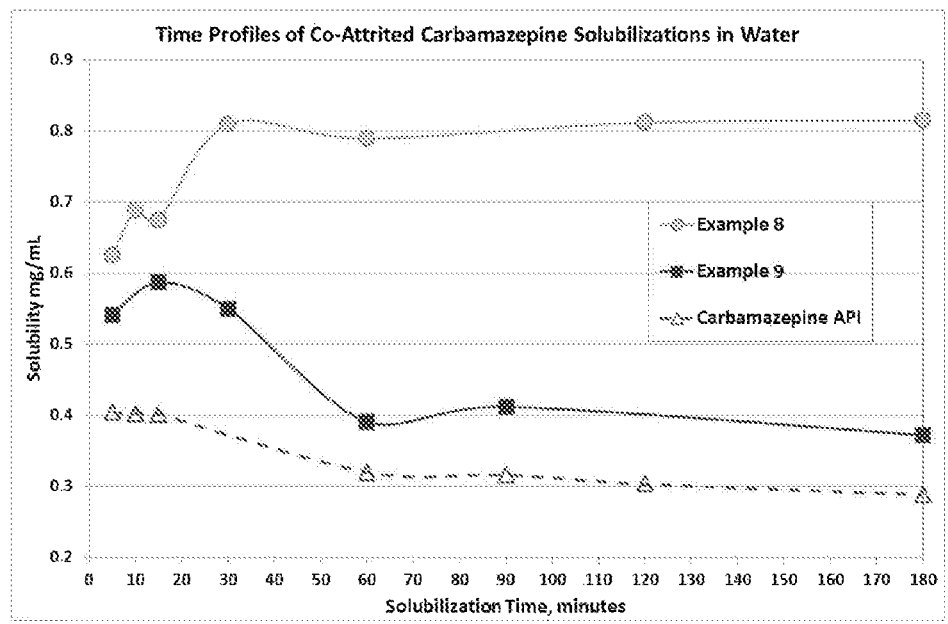
FIG. 2 illustrates the solubility time profiles of co-attrited Carbamazepine API with various excipients.

FIG. 2 further illustrates the solubility time profiles of Example 8 and Example 9 vs. the API control. It is shown that Example 9 seems to display a "Spring and Parachute" pattern as often encountered by the widely investigated "amorphous drug solid dispersions" as prepared by the conventional hot melt extrusion method or by the solvent-dispersion/spray drying method, albeit achieved herein by the present invention method.

It is a surprise discovery, however, to notice the pattern of Example 8 which provides a substantially improved API drug solubility or super-saturation, while delivering a very stable and smooth solubility curve over the 3 hours testing period.

Example 13 Co-Attrition of Carbamazepine, Soluplus and Povidone

A mixture of 600 gram of Carbamazepine, 350 gram of Soluplus, and 250 gram of Kollidone K30 was mixed in a Hobart Mixer while being sprayed with 150 gram of DI water. This substantially dry mixture was fed into a KRC Kneader for a few passes with indirect water cooling through the kneader jacket. The torque was maintained between 37 N.m to 150 N.m by adjusting the material feed rate. The kneader temperature was maintained between 25.7° C. to 41.8° C. range. After kneading, the extrudant was milled by a coffee bean grinder into powder and pass through a 80 mesh screen for down stream solubility testing.

Example 14 Solubility Time Profile of Co-Attrited Carbamazepine at 25° C.

A given amount of the co-attrited carbamazepine powder from Example 13 was put into 500 mL DI water inside a glass jar container equipped with a paddle stirring at 100 rpm which is placed at a 25° C. constant temperature control bath for 120 minutes. At each time interval, a given amount of solution was sampled and tested by an HPLC method. For reference, the API Carbamazepine was also tested for comparisons. The solubility results, in terms of drug concentration (μg/mL), are shown below.

TABLE 6

| Time (minutes) | API Carbamazepine (μg/mL) | Invention Sample (μg/mL) | Solubility Improvement, by |
|---|---|---|---|
| 5 | 89.167 | 219.29 | 146% |
| 10 | 175.64 | 276.36 | 57% |
| 15 | 225.68 | 288.95 | 28% |
| 30 | 202.16 | 299.23 | 48% |
| 45 | 175.05 | 296.46 | 69% |
| 60 | 172.69 | 307.14 | 78% |

TABLE 6-continued

| Time (minutes) | API Carbamazepine (μg/mL) | Invention Sample (μg/mL) | Solubility Improvement, by |
|---|---|---|---|
| 90 | 160.02 | 315.35 | 97% |
| 120 | 153.69 | 319.71 | 108% |

The foregoing embodiments and examples are provided for illustration only and are not intended to limit the scope of the invention. Various changes and modifications to the disclosed embodiments will be apparent to those skilled in the art based on the present disclosure, and such changes and modifications may be made without departure from the spirit and scope of the present invention. All references cited are incorporated by reference in their entirety.

What is claimed is:

1. A method of increasing solubility of an active pharmaceutical ingredient (API), comprising co-attriting a dry or substantially dry mixture of the API and a solubility-enhancing excipient with a kneading or extrusion device without heating, and if needed, applying cooling to the device to maintain temperature below the melting point of the API to form a co-attrition mixture, and applying an attrition force sufficient to increase the API solubility by at least 20%, wherein the API content in the co-attrition mixture ranges from 10% to 90% by weight, and wherein the co-attrition mixture is a solid or semi-solid dispersion comprising the API in a crystalline or partially crystalline form.

2. The method of claim 1, wherein the co-attriting is carried out by a co-attrition device selected from the group consisting of kneaders, kneading mixers, kneading extruders, extruders, or a modified hot melt extruder with a substantially augmented kneading/mixing action where no external heating is added and the API is not hot melted.

3. The method of claim 2, wherein the co-attrition device is a co-rotating twin screw kneader or extruder, or an equivalent thereof, optionally with indirect or direct cooling.

4. The method of claim 1, wherein peak co-attrition torque force of the co-attrition is at least 30 N.m.

5. The method of claim 1, wherein the API is a BCS Class II or Class IV poorly soluble drug substance.

6. The method of claim 1, wherein the API is a heat-sensitive drug molecule which would thermally degrade at its hot melting temperature if processed with a conventional hot melt extruder or has a high melting temperature that could not be reached by a conventional hot melt extruder device.

7. The method of claim 1, wherein the API is a heat-sensitive biopharmaceutical or a peptide and protein drug substance, wherein a protective layer or target chemical surface can be imparted onto the API by the co-attrition process.

8. The method of claim 1, wherein the substantially dry co-attrition mixture has a moisture content less than 30% by weight.

9. The method of claim 1, wherein the solubility enhancing excipient of the co-attrition mixture is selected from the group consisting of: polyvinylpyrrolidones (Povidones), polyvinylpyrrolidone derivatives or co-polymers (Copovidones), polyvinyl caprolactam-polyvinyl acetate-polyethylene glycol graft co-polymer, Crospovidones, polyethyleneglycols (PEG), PEG ether and ester derivatives or co-polymers, Poloxamers (polyethylene-propyleneglycols), carboxymethyl cellulose and salts (CMC), cross-linked CMCs (Croscarmellose), HPMCAS (Hypromellose acetate succinates), HPMC (hydroxypropyl methyl cellulose), hydroxyethyl cellulose, hydroxypropyl cellulose, ethyl cellulose, methyl cellulose, beta-cyclodextrins, hydroxypropyl beta-cyclodextrins, polyethyleneoxide polymers, polyvinyl alcohols, colloidal microcrystalline cellulose/carboxymethylcellulose, microcrystalline cellulose, HPMCP (hydroxypropylmethyl cellulose phthalates), polyethylene glycol-polyvinyl alcohol co-polymers, acrylic and methacrylic polymers or co-polymers and derivatives, Cholestyramine resins, Polacrilex resins, sodium polystyrene sulfonates and co-polymers, Polacrilin potassium, starches and modified starch derivatives, hydroxypropyl pea starch, maltodextrins, alginates, pectins, carregeenans, Xanthan gum, guar gums, proteins, sugars, sugar alcohols, heparin, gelatins, chitosan, lipids, phospholipids, lecithin, phosphatidylcholine, and combinations thereof.

10. The method of claim 1, wherein the solubility enhancing and stabilization excipients is selected from the group consisting of co-processed microcrystalline cellulose/carboxymethyl cellulose, povidones, poloxamers, polyvinyl caprolactam-polyvinyl acetate-polyethylene glycol graft co-polymer, HPMC, and combinations thereof.

11. The method of claim 1, wherein the co-attrition mixture further comprises an attrition aid and/or dispersing agent selected from the group consisting of organic and inorganic particles, water-soluble salts, and water-insoluble salts.

12. The method of claim 11, wherein the attrition aid or dispersing agent is selected from the group consisting of calcium carbonates, clays, calcium phosphates, calcium citrate, calcium silicates, silica, TiO2, alumina, microcrystalline cellulose, microcrystalline cellulose co-processed or blended with other excipients, powder cellulose, cellulose acetates, starches, chitin and chitosan, talc, micronized or colloidal metals, calcium chloride, calcium lactate, sodium chloride, potassium chloride, inorganic or organic ammonium salts, and combinations thereof.

13. The method of claim 1, wherein the co-attrition mixture further comprises an auxiliary pharmaceutical ingredient.

14. The method of claim 13, wherein the auxiliary pharmaceutical ingredient is selected from the group consisting of flavoring agents, coloring agents, pigments, sweeteners, taste-masking agents, penetrants, stabilizers, emulsifiers, surfactants, defoamers, lubricants, glidants, enzyme barriers or inhibitors (for protein and peptide drug protections), binders, disintegrants, and combinations thereof.

15. The method of claim 1, combined with an upstream or downstream pharmaceutical processing method, and/or a pharmaceutical dosage form manufacturing process.

16. A pharmaceutical composition or dosage form comprising an API processed according to a method of claim 1, wherein the API is poorly soluble drug substance or heat-sensitive drug substance, possesses enhanced solubility and/or bioavailability and maintains bioactivity in the extruded or kneaded mixture; and wherein the API solubility is increased by at least 20%.

17. The pharmaceutical composition or dosage form of claim 16, which is selected from the group consisting of antitumor drugs, anticancer drugs, antiviral drugs, antibacterial drugs, antifungal drugs, allergy drugs, cardiovascular drugs, anti-hypertension drugs, dermatology drugs, anti-protozoa drugs, anti-diabetes drugs, internal medicine drugs, nerve system drugs, mental health drugs, anti-seizure drugs, anti-epilepsy drugs, anti-depression drugs, pain relief drugs, flu relief drugs, pulmonary system drugs, respiratory system drugs, metabolism drugs, anti-attention disorder drugs, pediatric drugs, geriatric drugs, anti-aging drugs, anti-obesity drugs, cholesterol lowering drugs, anti-arthritis drugs, reproductive medicines, urinary system drugs, women's health drugs, hematology drugs, gastroenterology drugs, chemotherapy drugs, radiation therapy drugs, hormone therapy drugs, immunization drugs, anti-Aids, anti-inflammatory drugs, protein and peptide drugs, nucleotides, anesthetic drugs, psychotropic drugs, abuse prevention drugs, and organ transplant anti-rejection drugs.

18. The pharmaceutical composition or dosage form of claim 16, which is selected from the group consisting of: anticancer drugs; hormone drugs, anesthetic drugs, psychotropic drugs, abuse prevention drugs, antiviral drugs, antifungal drugs, antibacterial drugs, protein drugs, and nucleotides.

19. The pharmaceutical composition or dosage form of claim 16, which is a veterinary or animal drug product for birds, mammals, reptiles, fish, or crustaceous species; a herbal medicine; a Chinese medicine; or a Tibetan medicine application.

20. The pharmaceutical composition or dosage form of claim 18, wherein: the anticancer drug is selected from nilotinib, paclitaxel, cladribine, and altretamine; the hormone drug is selected from danazol, spironolactone, and fulvestrant; the anesthetic drug, psychotropic drug, or abuse prevention drug is selected from alprazolam, oxazepam, carbamazepine, and aripiprazole; the antiviral drug is selected from nevirapine, efavirenz, lopinavir, and ritonavir; the antifungal drug is selected from griseofulvin, posaconazole, and miconazole; the antibacterial drug is selected from rifampicin, sulfamethoxazole, and cefpodoxime proxetil; the protein drug is selected from leuprorelin, liraglutide, deoxyribonuclease, and superoxide dismutase; and the nucleotide is selected from fomivirsen, pegaptanib, and mipomersen.

* * * * *